United States Patent [19]

Schubert et al.

[11] 4,433,168
[45] Feb. 21, 1984

[54] PROCESS FOR THE PURIFICATION OF CRUDE 3,4,3',4'-TETRAAMINODIPHENYL

[75] Inventors: Hans Schubert, Kelkheim; Konrad Baessler, Frankfurt am Main, both of Fed. Rep. of Germany

[73] Assignee: Hoechst AG., Frankfurt, Fed. Rep. of Germany

[21] Appl. No.: 360,670

[22] Filed: Mar. 22, 1982

[30] Foreign Application Priority Data

Mar. 24, 1981 [DE] Fed. Rep. of Germany ....... 3111470

[51] Int. Cl.$^3$ .............................................. C07C 87/50
[52] U.S. Cl. .................................. 564/309; 564/407; 564/437
[58] Field of Search ........................ 564/309, 407, 437

[56] References Cited

U.S. PATENT DOCUMENTS

| | | | |
|---|---|---|---|
| 1,954,469 | 4/1934 | Booth | 564/407 |
| 2,036,134 | 3/1936 | Granacher et al. | 564/437 X |
| 2,062,349 | 12/1936 | Calcott et al. | 564/407 |
| 2,996,546 | 8/1961 | Spzigl | 564/309 |
| 3,134,813 | 5/1964 | Pelley | 564/424 |
| 3,390,180 | 6/1968 | Fontana et al. | 564/309 |
| 3,481,984 | 12/1969 | Orgen et al. | 564/309 |
| 3,865,876 | 2/1975 | Chenevey et al. | 564/407 |
| 3,943,175 | 3/1976 | Druin et al. | 564/407 X |
| 3,975,387 | 8/1976 | Schlicht et al. | 564/224 X |
| 4,255,356 | 5/1981 | Coenen et al. | 564/429 X |

FOREIGN PATENT DOCUMENTS 938629 10/1963 United Kingdom .

OTHER PUBLICATIONS

Chem. Abstracts 1973, vol. 78, Ref. 147537Z.

*Primary Examiner*—Robert V. Hines
*Attorney, Agent, or Firm*—Curtis, Morris & Safford

[57] ABSTRACT

Crude 3,4,3',4'-tetraaminodiphenyl (TAD) prepared by ammonolysis of 3,3'-dichlorobenzidine in the presence of mainly Cu catalysts is purified by a process in which
(a) after its isolation from the preparation process crude TAD is treated with an aqueous $NH_3$ solution and, if desired, TAD thus treated is then
(b) dissolved and reprecipitated in water in the presence of adsorbents and also of a water-soluble reducing agent.

Compared with relevant processes of the state of the art, the process produces a higher yield of pure TAD and it is also simpler to carry out.

10 Claims, No Drawings

PROCESS FOR THE PURIFICATION OF CRUDE 3,4,3',4'-TETRAAMINODIPHENYL 3,4,3',4'-Tetraaminodiphenyl—abbreviated to TAD in the text below—is a valuable intermediate and final product in various areas. TAD is used as an intermediate product, for example, in the preparation of polymers which are resistant to high temperatures, such as, for example, poly-2,2'-(m-phenylene)-5,5'-bibenzimidazole (compare U.S. Pat. Nos. 2,895,948 and 3,174,947); TAD is a final product, for example, when used as an antioxidant and as an agent for stabilizing epoxide resins.

TAD can be prepared by various known methods. One such known method is the ammonolysis of 3,3'-dichlorobenzidine—abbreviated to DCB in the text below—in the presence of mainly Cu catalysts (not only Cu compounds but also elementary Cu):

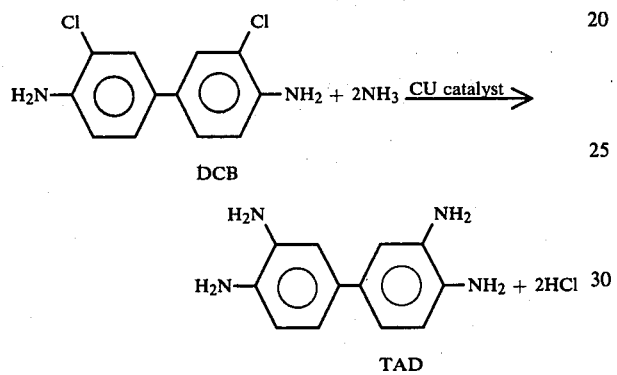

This ammonolysis is in general carried out by means of an aqueous $NH_3$ solution.

French Patent Specification No. 1,475,631 describes such an ammonolysis of 3,3'-dihalogenobenzidines, preferably DCB, in the presence of a Cu-I salt and/or of $Cu_2O$ and also of an alkaline earth metal salt (preferably $CaCl_2$) at an elevated temperature (100° to 250° C., preferably 150°-210° C.) and under an elevated inert gas pressure. Crude TAD thus obtained is purified via its salt with a strong acid. Yield data given are at about 70% of theory.

As comparative examples (Example 3 or 7 respectively) contained in the two U.S. Pat. Nos. 3,865,876 and 3,943,175 demonstrate, the process of the abovementioned French Patent Specification produces, before purification via a corresponding salt, a yield of crude TAD of about 82% (=202 g) at a product purity of 82% (according to a comparative example=Example 3 of U.S. Pat. No. 3,865,876); 62.9% of TAD still containing considerable amounts of Cl and Cu is then said to be obtained from this crude product via the HCl by means of a subsequent neutralization with NaOH (according to a comparative example=Example 7 of U.S. Pat. No. 3,943,175).

The process of U.S. Pat. No. 3,865,876 is said to achieve an improvement on this not very satisfactory result of the method in accordance with the abovementioned French Patent Specification by using essentially only Cu-I chloride as a catalyst in the ammonolysis of DCB. Here the yield data are at about 75 to 82% of theory of a product having a purity between about 85 and 87%.

This product, which has a Cu content of about 3 to 6% by weight, is said to be purifiable by the process of U.S. Pat. No. 3,943,175 (according to the examples of which, Cu-I chloride/Cu powder can also be used as a catalyst, in addition to Cu-I chloride), in which the product is purified advantageously via the sulfate (precipitation of TAD sulfate by means of sulfuric acid, isolation of the sulfate and liberation therefrom of TAD by means of a base) and, if desired, the TAD thus liberated is dissolved and reprecipitated from an aqueous solution; advantageously with addition of adsorbents, such as, for example, active charcoal and diatomaceous earth. According to the data given in this U.S. Patent Specification, the Cu content of TAD after the precipitation as the sulfate and liberation by means of a base is about 0.6 to 0.9%, and after the subsequent dissolving and reprecipitating, about 0.01 to 0.07%. The yield of TAD thus purified is here at most 51.9%, relative to crude TAD employed (compare Table 2, Run 6), or at most 45.7% of theory, relative to DCB employed (calculated from the values given).

The ammonolysis of DCB in accordance with Japanese Published Specification Nos. 74/11,212 and 74/11,213 is similar to the TAD preparation and purification processes given in U.S. Pat. Nos. 3,865,876 and 3,943,175 and is carried out in the presence of elementary Cu or of a Cu oxide or a Cu salt followed by a purification via a salt of an inorganic acid.

Because considerable losses of material are incurred in the known processes for the purification of crude TAD and also because the effort required to carry out these processes is not inconsiderable, the object was to improve these processes or to provide a new, improved purification process.

This object is achieved according to the invention, by treating Cu-containing crude TAD after its isolation from the preparation process with an aqueous $NH_3$ solution and, if TAD thus treated is also dissolved and reprecipitated in water in the presence of adsorbents, adding a water-soluble reducing agent.

The invention thus relates to a process for the purification of crude TAD prepared by ammonolysis of DCB in the presence of mainly Cu catalysts,
 (a) by treatment of crude TAD with an aqueous solution and, if desired,
 (b) dissolving and reprecipitating TAD thus treated in water in the presence of adsorbents;
which process comprises
 (a) treating crude TAD after its isolation from the preparation process with an aqueous $NH_3$ solution and
 (b) also adding a water-soluble reducing agent when TAD thus treated is dissolved and reprecipitated in water in the presence of adsorbents.

Using crude TAD having a Cu content between about 3 and 6% by weight as a starting material this process achieves at least about the same Cu content in the purified final product as the processes of U.S. Patent Specification 3,943,175 (after stage $a \leq 0.6$ to about 0.9% of Cu, and after the additional stage $b \leq 0.01$ to about 0.07% of Cu); however, after the purification process according to the invention the yield of pure TAD after the two purification stages is about 25% higher (about 77%) than in the process of the U.S. Patent Specification mentioned (at most 51.9%), relative to crude TAD employed. In addition, the treatment, according to the invention, of crude TAD by means of an aqueous $NH_3$ solution can be carried out in a considerably simpler manner than, for example, a state of the art precipitation of TAD by means of a strong mineral acid and a subsequent treatment with a base. The addition of a water-soluble reducing agent in stage b of the process according to the invention produces in particular a paler product than is produced solely by dissolving and reprecipitating in water in the presence of adsorbents but without a water-soluble reducing agent.

The manner is which it is carried out and the success in particular of stage (a) of the process according to the invention were not at all obvious and were extraordinarily surprising. That the Cu content of crude TAD is lowered in this process stage is probably due to Cu compounds being dissolved out in the form of $NH_3$ complexes. However, since the preparation of TAD by ammonolysis of DCB is carried out by means of not inconsiderable amounts of excess concentrated aqueous $NH_3$ solution, it had to be assumed that all Cu compounds convertible into soluble $CuNH_3$ complex compounds are thus converted into such soluble complex compounds, which are then washed out with water after the isolation of crude TAD obtained. It was quite unexpected that a treatment at this point with an aqueous $NH_3$ solution of crude TAD isolated after the preparation process could nevertheless produce a drastic lowering of the Cu content.

The improvement in the color of the product effected by the addition of a water-soluble reducing agent in stage (b) was also no longer to be expected since it could be assumed that virtually all materials responsible for the discolorations are removed by the presence of adsorbents.

The crude TAD employed as a starting material in the purification process according to the invention is a product prepared in accordance with relevant processes of the state of the art (as described at the outset) by ammonolysis of DCB in the presence of catalysts which are mainly composed of Cu compounds and, if appropriate, also of Cu metal. A preferred starting material is crude TAD prepared by the process of U.S. Pat. No. 3,943,175 (without the purification given there) in the presence, as a catalyst, of mainly only Cu-I chloride and, if appropriate, of elementary Cu. The product can be used in the state in which it is obtained in the preparation process, that is to say still in a form moist with mother liquor. However, crude TAD isolated after the preparation process from the mother liquor by means of a pressure filter or by using a (skimmer) centrifuge is preferably used.

The Cu content of crude TAD obtained by the known processes mentioned and correspondingly isolated is in general between about 3 and 6% by weight. To ensure the success of the process according to the invention it is advantageous that crude TAD supplied to the process after its isolation from the preparation process (by filtering off, filtering off with suction, centrifuging and the like) is not washed out with water beforehand.

The treatment of crude TAD after its isolation from the preparation process with an aqueous $NH_3$ solution in accordance with stage (a) of the process according to the invention is advantageously carried out by washing out with aqueous ammonia at room temperature and under atmospheric pressure. An aqueous $NH_3$ solution is generally used in this case which has an $NH_3$ concentration between about 10 and 28% by weight, preferably of about 20 to about 28% by weight. If the treatment is carried out under pressure (this is possible in principle), the $NH_3$ concentration can also be above about 28% by weight.

When the treatment is carried out at room temperature, quantities, per 100 g of crude TAD, of aqueous $NH_3$ solution within the concentration range of about 10 to 28% of about 50 to 1,000 ml are adequate; about 200 to 400 ml of an aqueous $NH_3$ solution in the preferred concentration range of about 20 to 28% are required.

After the treatment according to the invention with an aqueous $NH_3$ solution, TAD is normally washed with water until neutral. The Cu content of crude TAD thus treated is usually at least of the same order of magnitude as the Cu content (about 0.6 to 0.9%) of a product purified via the sulfate in accordance with the process of U.S. Pat. No. 3,943,175, but usually it is lower. When the process is carried out with care, even Cu contents of about 0.2% and lower can be achieved.

For some purposes for which TAD is used, lowering the Cu content to values of about 0.2% can be adequate. In these cases no further treatment is then necessary.

However, in general even Cu contents as low as about 0.2% are still a considerable nuisance. In these cases, stage (b) of the process according to the invention must subsequently also be carried out. This stage comprises dissolving and reprecipitating crude TAD purified in accordance with stage (a) in water in the presence of adsorbents and also of a water-soluble reducing agent. This dissolving and reprecipitating is in principle carried out as described in U.S. Patent Specification 3,943,175 for the case where no water-soluble reducing agent is used. TAD from stage (a) of the process according to the invention is thus accordingly dissolved in boiling water. Customary adsorbents, such as, for example, active charcoal, diatomaceous earth, kieselguhr and the like—preferably active charcoal having a surface area of about 1,100 to 1,200 $m^2/g$—are added to the solution. The amount of adsorbent is normally between about 10 and 30% by weight, preferably between about 15 and 25% by weight, relative to crude TAD (dry).

Additionally also a water-soluble reducing agent, such as, for example, an alkali metal sulfite, an alkali metal sulfide, an alkali metal dithionite and the like— preferably sodium dithionite, $Na_2S_2O_4$,—is added to this solution in accordance with the invention. If a dithionite is used, it is advantageous to employ it in a quantity of about 2 to 10% by weight, preferably about 2 to 3% by weight, relative to crude TAD (dry).

It is advantageous to boil the aqueous solution or suspension of stage (b) of the process according to the invention under reflux for a short time—preferably about 1 to 1.5 hours. The solution or suspension is then filtered and the filtrate is stirred until it has cooled to about room temperature. This produces almost colorless to slightly sand-colored pure TAD which has a Cu content of at least the same order of magnitude as the Cu content (about 0.01 to 0.07% of Cu) of TAD obtained by the process of U.S. Pat. No. 3,943,175, but usually lower. When the process is carried out with care Cu contents of about 0.005% by weight and below can be achieved. The melting point of the product is at 177° to 180° C. (according to the literature: 179° to 182° C.). Yields of pure TAD up to about 77% of theory, relative to the starting crude TAD (dry), can thus be achieved without difficulty. Because of the high oxygen sensitivity of TAD, all operations of the process according to the invention must be carried out with oxygen being excluded—that is to say under an inert gas (preferably nitrogen) atmosphere—to avoid a lowering of the yield.

The purification process according to the invention represents a considerable advance in this field, mainly because compared with relevant processes of the state of the art (U.S. Pat. No. 3,943,175!) the yield is about 25% higher and the manner in which the process is carried out is simpler.

The example which follows is intended to illustrate the invention in more detail. This is followed by a comparative example which demonstrates that it is vitally important to carry out the treatment according to the invention of crude TAD with aqueous $NH_3$ solution before it is washed with water until neutral.

Parts indicated in the example of the invention and in the comparative example are parts by weight. All operations in the preparation and purification of TAD were carried out under an atmosphere of nitrogen.

EXAMPLE

Preparation of TAD (according to the state of the art)

222 parts of moist DCB ($H_2O$ content of 19.7%), 27.7 parts of $Cu_2Cl_2$, 8.9 parts of Cu bronze or Cu powder and 1,179 parts of a 25% strength aqueous $NH_3$ solution were initially introduced into a 2 l V4A stainless steel autoclave, and air present in the autoclave was removed by twice injecting and releasing 20 to 25 bars of $N_2$. Thereafter 94 parts of liquid $NH_3$ ($d_{20}$:0.61) were also injected and the autoclave was heated for 7 hours at 200° C., during which period the pressure decreased from an initial value of 55 bars to about 50 bars. After the reaction period was complete, and after cooling to 25° C. and releasing the pressure, the autoclave content was forced through a pressure filter. Yield: 200 g of crude TAD (moist) = 141 g (dry).

(a) Treatment according to the invention of crude TAD with aqueous $NH_3$ solution Crude TAD (200 g), moist with mother liquor, was washed successively with about 500 parts of an approximately 25% strength aqueous $NH_3$ solution in 2 portions of 250 parts each and with 1,000 parts of $H_2O$ in 2 portions in each case.

Yield of TAD (dry): 136 g=96.5% of theory, relative to crude TAD;
Cu content: about 0.7%
Melting point: 175°–177° C.

The use of a skimmer centrifuge instead of the pressure filter to isolate the crude TAD produced virtually the same values, except for the Cu content (in this case: about 0.2%).

(b) Dissolving and reprecipitating, according to the invention

To dissolve and reprecipitate TAD obtained, 4 l of water, 30 parts of active charcoal (Carboraffin C or P type from Messrs. Lurgi) and 199 parts of TAD (from stage (a)) having an $H_2O$ content of about 30% were initially introduced into a 6 l stirred flask, the air was removed by twice evacuating and charging with $N_2$, 3 parts of $Na_2S_2O_4$ were then also added and the mixture was heated at the boil for 1 to 1.5 hours while stirring. The active charcoal was then pressure-filtered while the mixture was still hot, washed with about 150 ml of hot water and the filtrate was stirred after the addition of 1 part of $Na_2S_2O_4$ until it had cooled to about 25° C. Pure TAD which had crystallized out was filtered off with suction under an $N_2$ atmosphere and dried in vacuo. The resulting pure TAD had a color which was white to slightly sand-colored.

Yield of pure TAD: 107 g=75.9% of theory, relative to crude TAD, or 71.3% of theory, relative to DCB.
Cu content: ≦0.005%
Melting point: 177°–178° C.

COMPARATIVE EXAMPLE

For comparison the procedure of Example 1 was followed, but TAD (crude) which had been pressure-filtered and washed with 25% strength aqueous $NH_3$ solution was dissolved and reprecipitated in the absence of $Na_2S_2O_4$. The resulting TAD (pure) had a gray to dark gray color.

Yield pure: 107 g=75.9% of theory, relative to crude TAD, or 71.3% of theory, relative to DCB.
Cu content: 0.006%
Melting point: 177°–178° C.

We claim:

1. A method for purifying crude copper-contaminated 3,4,3',4'-tetraaminodiphenyl (TAD), directly isolated from a reaction mixture in which it has been prepared by the ammonolysis of 3,3'-dichlorobenzene with excess ammonia and in the presence of a catalyst containing copper, which method consists essentially of
   (1) washing said isolated crude TAD with an aqueous solution of $NH_3$ and
   (2) subsequently washing the ammonia-washed TAD with water until it is neutral.

2. A method as in claim 1, wherein said aqueous solution of $NH_3$ contains approximately 10 to 28 percent by weight of $NH_3$.

3. A method as in claim 1, wherein said aqueous solution of $NH_3$ contains approximately 20 to 28 percent by weight of $NH_3$.

4. A method for purifying crude copper-contaminated 3,4,3',4'-tetraaminodiphenyl (TAD), directly isolated from a reaction mixture in which it has been prepared by the ammonolysis of 3,3'-dichlorobenzene with excess ammonia and in the presence of a catalyst containing copper, which method consists essentially of
   (1) washing said isolated crude TAD with an aqueous solution of $NH_3$,
   (2) subsequently washing the ammonia-washed TAD with water until it is neutral,
   (3) then dissolving the washed, neutral TAD by heating in water containing an absorbent and an effective amount of a water-soluble reducing agent, and
   (4) precipitating the TAD from such an aqueous solution by cooling the solution.

5. A method as in claim 4, wherein said aqueous solution of $NH_3$ contains approximately 10 to 28 percent by weight of $NH_3$.

6. A method as in claim 4, wherein said aqueous solution of $NH_3$ contains approximately 20 to 28 percent by weight of $NH_3$.

7. A method as in claim 4, wherein said water-soluble reducing agent is selected from the group consisting of alkali metal sulfites, alkali metal sulfides, and alkali metal dithionites.

8. A method as in claim 4, wherein said water-soluble reducing agent is sodium dithionite.

9. A method as in claim 4, wherein said water-soluble reducing agent is present in an amount of about 2 to 3 percent by weight of said crude TAD, on a dry basis.

10. A method as in claim 4, wherein said water-soluble reducing agent is present in an amount of about 2 to 10 percent by weight of said crude TAD, on a dry basis.

* * * * *

UNITED STATES PATENT AND TRADEMARK OFFICE
CERTIFICATE OF CORRECTION

PATENT NO. : 4,433,168

DATED : February 21, 1984

INVENTOR(S) : Schubert et al.

It is certified that error appears in the above-identified patent and that said Letters Patent is hereby corrected as shown below:

Column 6, lines 23 and 39, "dichlorobenzene" should be --dichlorobenzidine--;

line 47, "absorbent" should be --adsorbent--.

Signed and Sealed this

Twelfth Day of July, 1988

Attest:

DONALD J. QUIGG

*Attesting Officer*  *Commissioner of Patents and Trademarks*